United States Patent [19]

Current

[11] 4,281,174

[45] Jul. 28, 1981

[54] OXIDATIVE CARBONYLATION OF ALCOHOLS TO PRODUCE DIALKYL OXALATES

[75] Inventor: Steven P. Current, Novato, Calif.

[73] Assignee: Chevron Research Company, San Francisco, Calif.

[21] Appl. No.: 141,840

[22] Filed: Apr. 21, 1980

[51] Int. Cl.³ .............................................. C07C 67/36
[52] U.S. Cl. .................................... 560/204; 560/190
[58] Field of Search ........................................ 560/204

[56] References Cited

U.S. PATENT DOCUMENTS

| | | | |
|---|---|---|---|
| 3,393,136 | 7/1968 | Fenton et al. | 560/204 |
| 3,994,960 | 11/1976 | Yamazaki et al. | 560/204 |
| 4,005,128 | 1/1977 | Zehner et al. | 560/204 |
| 4,005,129 | 1/1977 | Zehner | 560/204 |
| 4,005,130 | 1/1977 | Zehner | 560/204 |
| 4,076,949 | 2/1978 | Zehner | 560/204 |
| 4,118,589 | 10/1978 | Cassar et al. | 560/204 |

FOREIGN PATENT DOCUMENTS

| | | | |
|---|---|---|---|
| 2213435 | 10/1973 | Fed. Rep. of Germany | 560/204 |
| 51-95013 | 8/1976 | Japan | 560/204 |

OTHER PUBLICATIONS

Fenton et al., J. Org. Chem. 39(5) pp. 701–704 (1974).
Yamazaki et al., as cited in CA 85 176873f (1976).

*Primary Examiner*—Howard T. Mars
*Assistant Examiner*—Vera C. Clarke
*Attorney, Agent, or Firm*—D. A. Newell; T. G. Dejonghe; C. J. Caroli

[57] ABSTRACT

Preparation of dialkyl oxalates by the oxidative carbonylation of alcohols which comprises reacting a mixture of carbon monoxide and air with an alcohol in the presence of a catalytic amount of a catalyst comprising palladium in complex combination with a ligand, a small amount of a quinone, and a redox agent.

Advantageously the reaction is carried out in the presence of a solvent.

15 Claims, No Drawings

OXIDATIVE CARBONYLATION OF ALCOHOLS TO PRODUCE DIALKYL OXALATES

BACKGROUND OF THE INVENTION

This invention is concerned with an improved process for the oxidative carbonylation of alcohols to produce dialkyl oxalates and comprises the reaction of a mixture of carbon monoxide and oxygen with an alcohol in the presence of a catalytic amount of a catalyst comprising (1) palladium in complex combination with a ligand, (2) a quinone, such as benzoquinone, and (3) a redox agent.

The preparation of dialkyl oxalate esters by the reaction of carbon monoxide and alcohol is well known. U.S. Pat. No. 3,393,136 describes a process for the preparation of oxalates by contacting carbon monoxide at superatmospheric pressure, with a saturated monohydric alcohol solution of a platinum group metal salt and a soluble ferric or cupric salt (redox agent) while maintaining the salts in a highly oxidized state by the simultaneous introduction of oxygen or the application of a direct current electrical potential to the reaction zone. Water scavengers or dehydrating agents such as alkyl orthoformic acid esters must be added to the liquid phase to prevent the accumulation of water.

In an article by Donald M. Fenton and Paul J. Steinwand, *Journal of Organic Chemistry*, Vol. 39, No. 5, 1974, pp. 701-704, a general mechanism for the oxidative carbonylation of alcohols to yield dialkyl oxalates using a palladium redox system, oxygen and dehydrating agents has been proposed. In the absence of the necessary dehydrating agent, a large amount of carbon dioxide is formed and oxalates are not produced. The necessity of the iron or copper redox system during the oxalate synthesis is emphasized.

A West German Pat. No. 2,213,435 discloses a method for the synthesis of oxalic acid or oxalate esters using water or alcohol respectively. A platinum group metal salt, a salt of a metal more electropositive than the platinum group metal, e.g. copper (II) chloride and an alkali metal salt such as lithium chloride comprise the catalyst. Oxygen in stoichiometric amounts was employed as the oxidant. A disadvantage of such reaction is that explosive mixtures of oxygen and carbon monoxide are necessary to effect reaction. Alcohol conversion of less than 5 percent are obtained. Under non-explosive conditions only trace amounts of oxalate can be obtained.

U.S. Pat. No. 3,994,960 describes a process for the production of dialkyl oxalates by reacting an aliphatic alcohol with CO and oxygen under pressure in the presence of a catalyst of a mixture of a salt of a metal from the platinum group and a salt of copper or iron and a reaction accelerator including nitrates, sulfates, bicarbonates, carbonates, tertiary amines and hydroxides and carboxylates of alkali metals and alkaline earth metals, pyridine, quinoline, urea and thiourea. Conversion of the alcohol employed to the dialkyl oxalates in such process is low, generally less than 9 mole percent.

In a process similar to that of U.S. Pat. No. 3,994,960 above, West German Offenlegungschrift No. 2,601,139 shows the production of oxalic acid or its alkyl esters by reacting aliphatic alcohols or water with oxygen and carbon monoxide in the presence of palladium salts, redox salts and an amine or ammonia base.

U.S. Pat. Nos. 4,005,128 and 4,005,129 are concerned with the oxidative carbonylation of alcohols with carbon monoxide carried out in the presence of stoichiometric quantity of a metal oxide, such as copper or iron and a catalytic amount of a metal, such as palladium, platinum, copper, etc., and in the presence of an amine or an amine plus amine salt respectively.

U.S. Pat. No. 4,005,130 is concerned with a process for the preparation of oxalate esters by the oxidative carbonylation of alcohols with carbon monoxide in the presence of a catalytic amount of copper, nickel, cadmium, cobalt or zinc metal salt catalyst and at least a stoichiometric amount of an unsubstituted or halogen-substituted 2,5-cyclohexadiene-1,4-dione(1,4-benzoquinone). High yields and selectivity of the oxalate ester, over the carbonate ester and $CO_2$, are obtained and maximized by regulating temperature, carbon monoxide pressure and metal salt catalyst and by maintaining substantially anhydrous conditions.

U.S. Pat. No. 4,076,949 claims a process for the preparation of oxalate esters by reacting an alcohol with a mixture of carbon monoxide and oxygen in the presence of a catalytic mixture of:

(a) a palladium, rhodium, platinum, copper, or cadmium metal salt compound or mixture thereof;

(b) an aliphatic, cycloaliphatic, aromatic or heterocyclic amine or ammonium;

(c) a copper (I), copper (II), iron (II) or iron (III) oxidant salt compound; and (d) an ammonium or substituted ammonium salt compound or acid with a counterion other than a halide.

Alternatively, a ligand or coordination complex compound of the metal salt compound may be employed.

U.S. Pat. No. 4,118,589 relates to a proces for producing oxalic acid and esters of oxalic acid. More particularly, this patent describes a catalytic process for preparing oxalic acid and esters of same by the oxidative reaction, in a liquid phase, of carbon monoxide and water or alcohols with oxygen in the presence of redox systems. The catalyst systems used in accordance with the teaching of the patent comprise a redox catalyst consisting essentially of a salt of Pd (II) and salts of a metal more electropositive than Pd having at least two oxidation states and, optionally, salts of alkaline metals, and cocatalytic amounts of at least one base having the formula $R_2N$ in which the groups R, which may be like or unlike, are selected from the group consisting of hydrogen and alkyl radicals having from 1 to 10 carbon atoms.

The liquid oxalate esters are solvents, but the preferred use is as feedstock for hydrogenation to ethylene glycol.

SUMMARY OF THE INVENTION

The present invention provides a superior process for the production of dialkyl oxalates by the oxidative carbonylation of a normally liquid alcohol with a mixture of carbon monoxide and oxygen in the presence of a catalytic amount of a catalyst comprising (1) palladium in complex combination with a ligand, (2) a quinone, and (3) a redox agent. Mild reaction conditions of temperature and pressure effective to cause reaction of the alcohol and carbon monoxide to produce dialkyl oxalate are employed.

In accordance with the invention, the production of dialkyl oxalates in high yields and better selectivity is effected by carrying out the reaction of alcohol and carbon monoxide admixed with oxygen in the presence of a catalytic amount of a mixture comprising palladium in complex combination with a ligand, a quinone, and a redox agent, at a reaction temperature below about 100° C. and above about 50° C. and a reaction pressure of below about 1500 psi; and above about 500 psi. Yield and selectivity are further improved by the use of a selective solvent.

DESCRIPTION OF THE INVENTION

As hereinbefore mentioned, the present invention is based on the discovery that superior yields of dialkyl oxalates at better selectivities can be obtained from the reaction of an alcohol and a mixture of carbon monoxide, oxygen or oxygen-containing gas, such as air, in the presence of a palladium-containing catalyst, a quinone, and a redox agent. Reaction conditions of temperature and pressure are less severe than those encountered in the prior art. Substantial quantities of amines or amine salts or their mixtures are not required. Further, the use of quinone as a component in the catalyst mixture containing also palladium and redox agent is critical. Pursuant to the invention, a minimum amount of byproduct carbonate is formed, and yields of the order of 90–100 mol percent dialkyl oxalate can be obtained.

When oxidative carbonylation reactions of the type herein contemplated are conducted using palladium catalysts, with or without redox agents, and in the absence of the quinone component herein required, yields and selectivities are much lower. This is shown in the comparative experiments under Examples 3, 4, and 5.

The palladium-containing component of the catalyst mixture herein is formed by complexing a palladium source and a ligand using known methods, as described, for example, in U.S. Pat. No. 4,005,128, mentioned above and herein incorporated by reference.

Thus, suitable palladium sources for complexing include the palladium (II) compounds, for example palladium (II) sulfate, nitrate, carboxylates, such as acetate, propionate and oxalate; the palladium (II) halides, such as the chloride, bromide and iodide. Palladium compounds of valence state other than +2 are also suitable. Examples include tetrakis (triphenylphosphine) palladium (0), tris(dibenzylideneacetone) dipalladium (0), bis(triphenylphosphine)(1,4-benzoquinone) palladium (0). As indicated, palladium metal as such can also be used. Preferred are the palladium (II) carboxylates.

The ligands may be neutral or negatively charged. Neutral ligands are triorgano compounds of phosphorus, arsenic, antimony, or nitrogen. Suitable neutral ligands include alkyl phosphines such as trimethylphosphine and tributylphosphine, aryl-phosphines such as triphenylphosphine, mixed alkylaryl phosphines, such as diethylphenylphosphine, trialkylamines, such as triethylamine or 1,4-diamino-bicyclo[2.2.2] octane. Phophites, such as triphenyl phosphite or tributyl phosphite may also be employed. Other suitable neutral ligands include tetramethyl diphosphinoethane and tetraphenyl diphosphinoethane, as well as phosphorus-substituted polymers such as polymer-bound triphenyl phosphine on styrene-divinylbenzene copolymers. Exactly analogous derivatives of arsenic and antimony may be used; however, because of their greater ease of preparation and stability of the derived complexes, the derivatives of phosphorus are preferred.

The complex palladium compounds suitable for use in the process of the present invention may contain in the molecule, in addition to the ligands discussed above, one or more other atoms, groups or molecules, which are chemically bonded to the palladium atoms or atoms. Atoms which may be bonded to the metal include, for example, hydrogen, nitrogen and halogen atoms; groups which may be bonded to the palladium include, for example, hydrocarbyl, hydrocarbyloxy, carbonyl, nitrosyl, cyano and SnCl$_3$-groups; molecules which may be bonded to the palladium include, for example, organic isocyanides and isothiocyanates.

Examples of suitable complex compounds are those represented by the following formulae:
(Ph$_2$EtP)$_2$PdBr$_2$
(PhEt$_2$P)(CO)PdCl$_2$
(PhO$_3$P)$_2$Pd(OAc)$_2$
(Et$_3$As)$_2$Pd(OAc)$_2$
(Ph$_3$P)$_3$(CO)Pd
(Ph$_3$P)$_2$Pd(OAc)$_2$
(Ph$_3$P)$_2$PdI$_2$
*Pd$_2$(dba)$_3$.CHCl$_3$
(Ph$_3$P)$_4$Pd
*dba=dibenzylideneacetone Examples of negatively charged ligands are halide and pseudohalide salts, such as LiCl and LiI.

The complex compounds employed may be introduced into the reaction mixture as such, or they may be formed in situ from a palladium source noted above and the desired ligand.

The quinone component of the catalyst mixture is a cyclic diketone capable of being reduced to aromatic diols. It may be represented by the formula

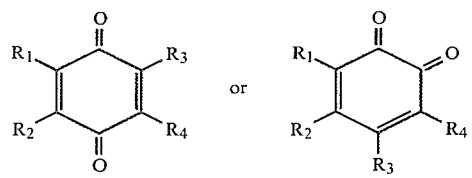

wherein R$_1$, R$_2$, R$_3$, and R$_4$ can be hydrogen, alkyl, aryl, halogen, alkoxy, or cyano, and wherein R$_1$ and R$_2$ or R$_3$ and R$_4$ can be connected to form a ring, provided that the total number of carbon atoms in the quinone does not exceed about 20. Specific examples of quinones are 1,4-benzoquinone and halogen-substituted 1,4-benzoquinones, including the mono-, di-, tri- and tetra-substituted chloro, bromo, fluoro and iodo compounds. In addition to 1,4-benzoquinone per se, representative halogen-substituted 1,4-benzoquinones include, for example, 2-chloro, 2-bromo-, 2-fluoro- and 2-iodo-1,4-benzoquinones, 2,5-, 2,6- and 2,3-dichloro-, dibromo, difluoro-, and diiodo-1,4-benzoquinones, 2,3,5-trichloro-, tribromo-, trifluoro-, and triiodo-1,4-benzoquinones and the 2,3,5,6-tetrachloro-1,4-benzoquinone(chloranil), 2,3,5,6-tetrabromo-1,4-benzoquinone(bromanil), 2,3,5,6-tetrafluoro- and 2,3,5,6-tetraiodo-1,4-benzoquinones. Additional examples are 1,4-naphthaquinone, 1,2-naphthaquinone, diphenoquinone, phenanthraquinone, 1,2-benzoquinone, 2,3,5,6-tetracyano-1,4-benzoquinone, 2,3,5,6-tetramethyl-1,4-benzoquinone. Mixtures of the quinones may also be employed. The preferred quinone is 1,4-benzoquinone.

The alcohols suitable for use in the process of the present invention and generally employed in at least stoichiometric quantities, are the monohydric saturated aliphatic and alicyclic alcohols and may contain other substituents such as halo, amido, alkoxy, amino, carboxy, cyano, etc. radicals in addition to the hydroxyl group. The substituents, in general, do not interfere with the reaction of the invention. The alcohols which may be primary, secondary or tertiary alcohols conform to the general formula ROH, wherein R is an optionally substituted aliphatic or alicyclic group preferably containing from 1 to 20 carbon atoms. In general, the satisfactory alcohol is one which is normally liquid under the conditions employed in the carbonylation reaction. Representative alcohols especially suitable for use in this invention are monohydric alcohols such as methyl, ethyl, n-iso-, sec-, and tert-butyl, amyl, hexyl, octyl, lauryl, n- and sec-propyl, cetyl, benzyl, chlorobenzyl and methoxybenzyl alcohols as well as, for example, cyclohexanol, octanols, heptanols, decanols, undecanols, 2-ethyl hexanol, nonanol, myristyl alcohol, stearyl alcohol, methyl cyclohexanol, pentadecanol, oleyl and eicosonyl alcohols, and the like. Preferred alcohols are the normally liquid monohydric alcohols having 1 to 6 carbon atoms.

The redox agent component of the catalyst mixture is well known to those skilled in the art. It is generally a compound of cobalt, manganese, copper, iron or vanadium. Particularly preferred are the compounds of cobalt. Examples include simple cobalt salts such as halides or carboxylates, or cobalt (II) complexes of organic ligands that are known to form complexes with molecular oxygen. Examples include:

N,N'-dipropylenmethylaminobis(salicylideneiminato) cobalt(II)
Co (salMedpt)

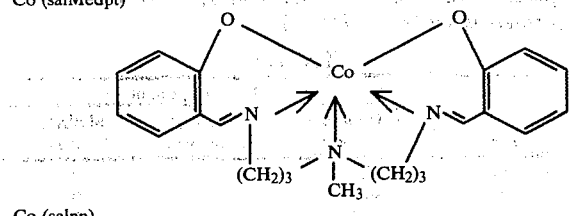

Co (salpn)

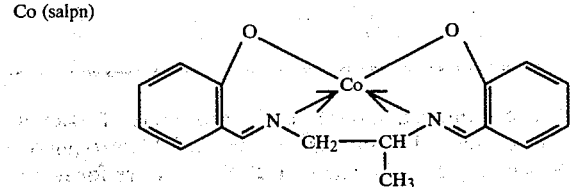

N,N'-methylethylenebis(salicylideneimato)cobalt(II)
Co (acacen)

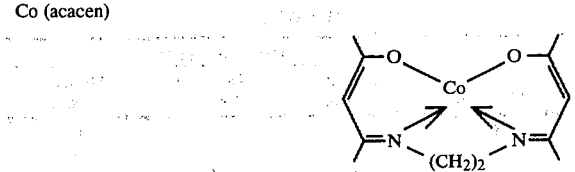

(4,4'-ethylenedinitrilodi-2-pentanonato)cobalt(II)

Other examples of redox agents are soluble ferric, ferrous, cupric or cuprous salts. Specifically there may be mentioned the carboxylates having 1 to 5 carbon atoms, e.g., cupric acetate, ferrous propionate, ferric acetate, cupric butyrate, etc.; halide salts, e.g., cupric chloride, ferric chloride, ferric bromide, cuprous chloride, cupric bromide, ferric iodide, ferric sulfate, ferric nitrate, cupric nitrate, etc. The preferred redox component of the catalyst is cobalt (II) acetate.

The reaction may be carried out in an autoclave or any other high pressure reactor. A general procedure is to charge the alcohol and catalyst mixture into the reactor vessel, introduce the proper amount of carbon monoxide and oxygen to obtain the desired reaction pressure and then heat the mixture at the desired temperature for the appropriate period. The reaction can be carried out batchwise or as a continuous process and the order of addition of the reactants may be varied to suit the particular apparatus employed. The reaction products are recovered and treated by any conventional method such as distillation and/or filtration, etc. to effect separation of the oxalate from unreacted materials, catalyts, oxidant, byproducts, etc. Initially the reaction is performed under relatively anhydrous conditions, but water is produced during the course of the reaction.

The reaction is generally carried out in the presence of a catalytic proportion of the palladium-redox agent-quinone mixture and will proceed with small amounts of the catalyst components hereinabove described. The amount of palladium-redox agent-quinone catalyst mixture ranges from about 0.1 to 5 weight percent of the alcohol used in the reaction, the preferred amount being 0.5 to 2 weight percent. Generally the proportions of the catalyst components used in the reaction will be equivalent to between about 0.1 to 1 mol, preferably 0.2 to 0.5 mol, of palladium in the palladium-containing catalyst per mol of quinone, 0.1 to 10 mols, preferably 0.2 to 0.5 mol, of palladium per mol of metal in the redox agent. In complexing the ligand with the palladium compound, the proportion of palladium compound and ligand is, based on palladium metal, in the range 0.1 to 1 mol, preferably 0.25 to 0.5, per mol of ligand.

The process of the invention is operated entirely under the liquid phase conditions of the anhydrous alcohol, oxidant and catalyst. Although not required, solvents, if desired, which are chemically inert to the components of the reaction system may be employed. Suitable solvents include, for example, hydrocarbons such as hexane, heptane, octane, toluene and xylene; ethers, such as tetrahydrofuran, diethylether; halogenated hydrocarbons, such methylene chloride, chloroform and dichlorobenzene; organic esters or diesters such as ethyl acetate, n-propyl formate, isopropyl acetate, sec- and isobutyl acetate, amyl acetate, cyclohexyl acetate, n-propyl benzoate, and lower alkyl phthalates; and nitriles, such as acetonitrile. The preferred method of operation is with excess alcohol used with the carbonylation reaction, functioning also as a solvent.

As indicated above, the reaction can be suitably performed by introducing the carbon monoxide and oxygen at a desired pressure into contact with the alcoholic reaction medium containing the specified alcohol and catalyst mixture and heating to the desired temperature. In general, carbon monoxide pressures of about 500 psi to about 1500 psi preferably 750 to 1250 psi may be employed. Excess quantities of carbon monoxide are generally employed. A suitable recycle of the carbon monoxide may be employed. The reaction will proceed at temperatures of from about 50° C. to 100° C. It is generally preferred to operate the process at temperatures in the range of 80° C. to 90° C. to obtain a convenient rate of reaction. Heating and/or cooling means may be employed interior and/or exterior of the reaction to maintain the temperature within the desired range.

At least stoichiometric amounts of oxygen or an oxygen-containing gas, such as air, are employed, the oxygen partial pressure being such as to avoid an explosive mixture. In accordance with the *Handbook of Chemistry and Physics,* 48th Edition, 1967, the explosive limits of pure oxygen in carbon monoxide is 6.1 to 84.5 volume percent and air in carbon monoxide is 25.8 to 87.5 volume percent. The volume percent of the oxygen in the oxygen-carbon monoxide mixture usually amounts to 3-6%. In carrying out the reaction the oxygen is charged to the reaction vessel to the desired pressure and concentration and for safety reasons may be charged in portions.

The reaction time is generally dependent upon the alcohol being reacted, temperature, pressure and on the amount and type of catalyst and oxidant being charged as well as the type of equipment being employed. Reaction times will vary dependent on whether the process is continuous or batch. The reaction is limited by the available oxidant, alcohol and carbon monoxide.

The following examples are provided to illustrate the invention in accordance with the principles of this invention but are not to be construed as limiting the invention in any way except as indicated by the appended claims.

EXAMPLES

In the Examples that follow the compound diglyme was used as the internal standard for the quantitative gas chromatography.

Example 1

A 300 ml stainless steel autoclave was charged with:
palladium (II) acetate (0.113 g, 0.50 mmol)
triphenyl phosphine (0.395 g, 1.51 mmol)
cobalt (II) acetate tetrahydrate (0.500 g, 2.01 mmol)
1,4-benzoquinone (0.271 g, 2.51 mmol)
methanol (16.0 g, 500 mmol)
diglyme (1.418 g, 10.566 mmol)
acetonitrile (to yield 100 ml total).

The autoclave was flushed with nitrogen and then charged with 1250 psi carbon monoxide followed by 75 psi oxygen. The reactor was stirred at 1600 rpm and heated to 90° C. Liquid samples were removed periodically and analyzed by quantitative gas chromatography. Products were formed as shown in Table 1. The time that the reactor reached 90° C. is defined as zero hours. For each 30 mmol of dimethyl oxadate formed, 100 psi carbon monoxide and 25 psi oxygen were added to the autoclave. After cooling the reactor, the gases were vented through a tube filled with Ascarite for the determination of carbon dioxide. A weight gain of 0.535 g (12.2 mmol of carbon dioxide) was noted.

TABLE 1

| Time, hr | products, mmol | | |
|---|---|---|---|
| | Dimethyl Oxalate | Dimethyl Carbonate | Methyl Formate |
| 0 | 18.8 | 0 | 0 |
| 0.5 | 38.9 | 0 | 0 |
| 1.0 | 50.6 | 0 | 0 |
| 2.0 | 58.5 | 0 | 0 |
| 5.0 | 67.3 | 0 | 0 |
| 7.0 | 70.1 | 0 | 0 |
| 11.0 | 70.7 | 0 | 0.8 |

Example 2

A 300 ml stainless steel autoclave was charged with:
palladium (II) acetate (0.113 g, 0.50 mmol)
triphenyl phosphine (0.394 g, 1.50 mmol)
cobalt (II) acetate tetrahydrate (0.0500 g, 2.0 mmol)
1,4-benzoquinone (0.270 L g, 2.50 mmol)
diglyme (1.347 g, 10.04 mmol)
methanol (to make 100 ml total).

The procedure of Example 1 was followed. Products in the liquid phase were determined by quantitative analysis by gas chromatography as indicated in Table 2. A total of 0.7 mmol of carbon dioxide was found in the gas phase at the end of the reaction.

TABLE 2

| Time, hr | Products, mmol | | |
|---|---|---|---|
| | Dimethyl Oxalate | Dimethyl Carbonate | Methyl Formate |
| 0 | 1.8 | 0 | 0 |
| 1 | 14.1 | 0 | 0 |
| 1.5 | 36.6 | 0.8 | 0 |
| 2 | 36.7 | 0.8 | 0 |
| 3 | 36.9 | 0.9 | 6 |

Example 3

A 300 ml stainless steel autoclave was charged with:
palladium (II) acetate (0.113 g, 0.50 mmol)
triphenyl phosphine (0.395 g, 1.51 mmol)
cobalt (II) acetate tetrahydrate (0.499 g, 2.00 mmol)
1,4-benzoquinone (0.270 g, 2.50 mmol)
methanol (16.0 g, 500 mmol)
diglyme (1.35 g, 10.03 mmol)
methylene chloride (to yield 100 ml total).

The procedure of Example 1 was followed. Liquid samples were withdrawn periodically and analyzed by quantitative gas chromatography. Products were formed as shown in Table 3.

TABLE 3

| Time, hr | Products, mmol | | |
|---|---|---|---|
| | Dimethyl Oxalate | Dimethyl Carbonate | Methyl Formate |
| 0 | 14.0 | 0 | 0 |
| 0.5 | 36.6 | 0 | 0 |
| 1.0 | 38.8 | 0 | 0 |
| 2.0 | 39.5 | 0 | 0 |
| 3.0 | 39.7 | 0 | 0 |

For comparative purposes the procedure of Example 3 was followed exactly except that no 1,4-benzoquinone was charged to the reaction. Products were formed as shown in Table 4.

TABLE 4

| Time, hr | Products, mmol | | |
|---|---|---|---|
| | Dimethyl Oxalate | Dimethyl Carbonate | Methyl Formate |
| 0 | 6.8 | 1.6 | 0 |
| 1.0 | 19.7 | 3.1 | Trace |
| 2.0 | 22.4 | 4.3 | 7.1 |
| 3.0 | 22.8 | 4.5 | 7.4 |

Example 4

A 300 ml stainless steel autoclave was charged with:
palladium (II) acetate (0.056 g, 0.25 mmol)
triphenyl phosphine (0.197 g, 0.75 mmol)
Co(salMedpt) (0.205 g, 0.50 mmol)
1,4-benzoquinone (0.270 g, 2.50 mmol)
methanol (32.0 g, 1.0 mmol)
diglyme (0.691 g, 5.15 mmol)
methylene chloride (to make 100 ml total).

The autoclave was flush with nitrogen and then charged with 1000 psi of carbon monoxide followd by 500 psi of air. The reactor was stirred at 1600 rpm and heated to 80° C. Liquid samples were withdrawn periodically or the determination of carbon and analyzed by quantitative gas chromatography. Products were formed as shown in Table 5.

TABLE 5

| Time, hr | Products, mmol | | |
|---|---|---|---|
| | Dimethyl Oxalate | Dimethyl Carbonate | Methyl Formate |
| 0 | 3.0 | 0 | 0.1 |
| 1.0 | 17.8 | 0 | 0.7 |
| 4.0 | 27.6 | 0.7 | 1.0 |
| 6.0 | 30.3 | 0.8 | 1.0 |

For comparative purposes the procedure of Example 4 was followed exactly except that no 1,4-benzoquinone was charged to the reactor. Products formed are shown in Table 6.

TABLE 6

| Time, hr | Products, mmol | | |
|---|---|---|---|
| | Dimethyl Oxalate | Dimethyl Carbonate | Methyl Formate |
| 0 | 1.2 | 0 | 0.1 |
| 1 | 7.0 | 0 | 0.6 |
| 4 | 14.7 | 1.2 | 1.0 |
| 5.5 | 16.9 | 1.3 | 1.3 |

Example 5

A 300 ml stainless steel autoclave was charged with:
palladium (II) acetate (0.112 g, 0.50 mmol)
cobalt (II) acetate tetrahydrate (0.498 g, 2.0 mmol)
lithium iodide (0.337 g, 2.52 mmol)
1,4-benzoquinone (0.271 g, 2.51 mmol)
diglyme (2.708 g, 20.17 mmol)
methanol (to make 100 ml total).

The autoclave was flushed with nitrogen and charged with 1250 psi of carbon monoxide followed by 75 psi of oxygen. The reactor was stirred at 1600 rpm. After 30 minutes at 90° C., quantitative analysis by gas chromatography indicated 33.5 mmol of dimethyl oxadate and 8.0 mmol of dimethyl carbonate had been formed.

For comparative purposes the procedure of Example 5 was followed except that no 1,4-benzoquinone was charged to the reactor. After 40 minutes, quantitative analysis by gas chromatography indicated that 28.9 mmol of dimethyl oxalate and 11.5 mmol of dimethyl carbonate had been formed.

Example 6

A 300 ml stainless steel autoclave was charged with:
palladium (II) acetate (0.112 g, 0.50 mmol)
triphenyl phosphine (0.393 g, 1.50 mmol)
cobalt (II) acetate tetrahydrate (0.499 g, 2.0 mmol)
1,2-naphthoquinone (0.396 g, 2.51 mmol)
methanol (16.0 g, 500 mmol)
diglyme (2.77 g, 20.65 mmol)
acetonitrile (to make 100 ml total).

The procedure of Example 1 was followed. The products were determined by quantitative gas chromatography as indicated in Table 7.

TABLE 7

| Time, hr | Products, mmol | | |
|---|---|---|---|
| | Dimethyl Oxalate | Dimethyl Carbonate | Methyl Formate |
| 0 | 21.1 | 0 | 1.0 |
| 0.5 | 27.7 | 0 | 1.1 |
| 1.0 | 30.7 | 0 | 1.2 |
| 3.0 | 34.4 | 0 | 1.2 |

TABLE 7-continued

| Time, hr | Products, mmol | | |
|---|---|---|---|
| | Dimethyl Oxalate | Dimethyl Carbonate | Methyl Formate |
| 3.5 | 34.9 | 0 | 1.4 |

Example 7

A 300 ml stainless steel autoclave was charged with:
palladium (II) iodide (0.180 g, 0.50 mmol)
Co(salMedpt) (0.820 g, 2.00 mmol)
lithium iodide (0.134 g, 1.00 mmol)
1,4-benzoquinone (0.271 g, 2.51 mmol)
methanol (16.0 g, 500 mmol)
diglyme (1.350 g, 10.06 mmol)
methylene chloride (to make 100 ml total).

The procedure of Example 1 was followed. Products were determined by gas chromatography and are indicated in Table 8.

TABLE 8

| Time, hr | Products, mmol | | |
|---|---|---|---|
| | Dimethyl Oxalate | Dimethyl Carbonate | Methyl Formate |
| 0.1 | 1.2 | 0 | 0 |
| 1.0 | 4.6 | 0.8 | 0 |
| 2.0 | 7.1 | 1.3 | 0 |
| 3.0 | 10.4 | 1.8 | 0.2 |

Example 8

A series of 11 ml stainless steel microreactors were each charged with:
palladium (II) acetate (0.01 mmol)
cobalt (II) acetate tetrahydrate (0.04 mmol)
triphenyl phosphine (0.03 mmol)
1,4-benzoquinone (0.05 mmol)
methanol (10.0 mmol)

A solvent was added (2.0 ml) as indicated in Table 9. The reactors were further charged with 750 psi carbon monoxide and 250 psi air. After heating at 90° C. with gentle shaking for 3 hours, the reactors were cooled and the products determined by gas chromatography as indicated in Table 9.

TABLE 9

| Solvent | Products, mmol | | |
|---|---|---|---|
| | Dimethyl Oxalate | Dimethyl Carbonate | Methyl Formate |
| methylene chloride | 0.18 | 0 | 0.05 |
| acetonitrile | 0.41 | 0 | 0.22 |
| methanol | 0.23 | 0 | 0 |
| dimethyl carbonate | 0.43 | | 0.05 |
| dimethyl sulfoxide | 0.01 | 0 | 0 |
| ethyl acetate | 0.45 | 0 | 0 |
| benzonitrile | 0.60 | 0 | 0 |
| toluene | 0.51 | 0 | 0 |
| tetrahydrofuran | 0.13 | 0 | 0 |
| triglyme | 0.37 | | 0.05 |
| tetraglyme | 0.33 | trace | trace |
| acetone | 0.35 | trace | trace |

Example 9

A 300 ml stainless steel autoclave was charged with:
palladium (II) acetate (0.5 mmol)
triphenyl phosphine (1.5 mmol)
1,4-benzoquinone (2.5 mmol)
methanol (500 mmol)

methylene chloride (to make 100 ml total) and a cobalt compound (2.0 mmol) as shown in Table 10. The reactor was further charged with carbon monoxide (1250 psi) and oxygen (75 psi), then heated with stirring to 90° C. After 2 hours, analysis by gas chromatography indicated the formation of dimethyl oxalate as shown in Table 10.

TABLE 10

| Cobalt Compound | Dimethyl Oxalate, mmol |
|---|---|
| Co(salMedpt) | 41 |
| Co(salpn) | 37 |
| Co(acacen) | 31 |

What is claimed is:

1. A process for preparing dialkyl oxalates by the oxidative carbonylation reaction which comprises contacting a normally liquid monohydric saturated aliphatic or alicyclic alcohol containing from 1 to 20 carbon atoms with a mixture of carbon monoxide and oxygen in the presence of a catalytic amount of a mixture comprising (1) palladium in complex combination with a neutral or negatively charged ligand, (2) a quinone, and (3) a redox agent comprising a compound of cobalt, manganese, copper, iron or vanadium, said contacting being conducted at a reaction temperature in the range of about 50° C.–100° C. and a carbon monoxide partial pressure in about the range 500 psi to 1500 psi.

2. A process according to claim 1, wherein the palladium and quinone are present in molar ratios of palladium to quinone in about the range 0.1 to 1, the palladium and redox agent in molar ratios of palladium to redox agent metal in about the range 0.1 to 10, the oxygen being present in an amount of about 3–6% by volume of the carbon monoxide-oxygen mixture.

3. A process according to claim 1, wherein the alcohol contains 1 to 6 carbon atoms.

4. A process according to claim 1, wherein the reaction is carried out in the presence of a solvent inert to the components of the reaction system.

5. A process according to claim 4, wherein the palladium and solvent are present in an amount of about 0.001 to 1 weight percent palladium based on the two.

6. A process according to claim 5, wherein the solvent is acetonitrile.

7. A process according to claim 1, wherein the redox agent is a cobalt compound.

8. A process according to claim 7, wherein the cobalt redox agent is cobalt acetate.

9. A process according to claim 1, wherein the palladium and quinone are present in molar ratios of palladium to quinone in about the range 0.2 to 0.5, the palladium and redox agent in molar ratios of palladium metal to redox agent metal in the range 0.2 to 0.5, the reaction temperature is in the range 80°–90° C., the carbon monoxide partial pressure is in about the range 750–1250 psi, the oxygen being present in an amount of 3–6% volume percent of the carbon monoxide-oxygen mixture.

10. The process according to claim 9, wherein the reaction is carried out in the presence of a solvent inert to the components of the reaction mixture, the amount of palladium and solvent being present in an amount of about 0.1 weight percent based on the two.

11. A process according to claim 10, wherein the solvent is acetonitrile and the alcohol has 1 to 6 carbon atoms.

12. A process according to claim 1, wherein the palladium is in complex combination with a triorgano compound of phosphorus, arsenic, antimony or nitrogen.

13. A process according to claim 12, wherein the molar ratio of palladium metal to triorgano compound is in about the range 0.1 to 1.

14. A process according to claim 13, wherein the palladium and quinone are present in molar ratios of palladium to quinone in about the range 0.1 to 1, the palladium and redox agent in molar ratios of palladium to redox agent metal in about the range 0.1 to 10, the reaction temperature is in the range about 50° C.–100° C., the carbon monoxide partial pressure is about the range 500 psi to 1500 psi, the oxygen being present in an amount about 3–6% volume of the carbon monoxide-oxygen mixture.

15. Process according to claim 14, wherein the alcohol contains 1 to 6 carbon atoms.

* * * * *

UNITED STATES PATENT AND TRADEMARK OFFICE
CERTIFICATE OF CORRECTION

PATENT NO. : 4,281,174

DATED : July 28, 1981

INVENTOR(S) : Steven P. Current

It is certified that error appears in the above-identified patent and that said Letters Patent are hereby corrected as shown below:

Column 7, line 67,"(0.270 L g, 2.50 mmol)" should read
--(0.270 g, 2.50 mmol)--.

Signed and Sealed this

Thirtieth Day of March 1982

[SEAL]

Attest:

GERALD J MOSSINGHOFF

Attesting Officer

Commissioner of Patents and Trademarks